(12) United States Patent
Katsura et al.

(10) Patent No.: US 7,132,548 B2
(45) Date of Patent: Nov. 7, 2006

(54) PROCESS FOR RECOVERING 1,3-DIMETHYL-2-IMIDAZOLIDINONE

(75) Inventors: Tadashi Katsura, Toyonaka (JP); Nobuhiro Arai, Nagaokakyo (JP); Tadashi Mizuno, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/129,357

(22) Filed: May 16, 2005

(65) Prior Publication Data

US 2005/0261505 A1   Nov. 24, 2005

(30) Foreign Application Priority Data

May 18, 2004   (JP) ............... 2004-147281

(51) Int. Cl.
*C07D 233/32*   (2006.01)

(52) U.S. Cl. .................................. 548/316.4

(58) Field of Classification Search ............. 548/316.4
See application file for complete search history.

(56) References Cited

FOREIGN PATENT DOCUMENTS

| JP | 03-038571 | 2/1991 |
| JP | 07/070080 | 3/1995 |
| JP | 11-152272 | 6/1999 |

*Primary Examiner*—Taofiq Solola
(74) *Attorney, Agent, or Firm*—Foley & Lardner LLP

(57) ABSTRACT

The present invention provides a process for recovering 1,3-dimethyl-2-imidazolidinone comprising extracting 1,3-dimethyl-2-imidazolidinone from an aqueous solution containing it with n-butanol in the presence of an inorganic salt to obtain n-butanol layer and, subjecting the n-butanol layer to distillation.

As 1,3-dimethyl-2-imidazolidinone can be recoverable at high purity from an aqueous solution containing 1,3-dimethyl-2-imidazolidinone easily and efficiently without using alkali, the present process is industrially advantageous.

4 Claims, No Drawings

PROCESS FOR RECOVERING 1,3-DIMETHYL-2-IMIDAZOLIDINONE

This nonprovisional application claims priority under 35 U.S.C. § 119(a) on patent application Ser. No. 2004-147281 filed in JAPAN on May 18, 2004, the entire contents of which are hereby incorporated by reference.

BACKGROUND OF THE INVENTION

1. Field of the Invention

The present invention relates to a process for recovering 1,3-dimethyl-2-imidazolidinone.

2. Prior Art 1,3-Dimethyl-2-imidazolidinone is an aprotic polar solvent with excellent acid- and alkaline-resistance, and is frequently used as a solvent for various kind of organic synthetic reactions (ex. JP-A-6-192156, JP-A-11-12253, JP-A-2002-121186, JP-A-2002-293766, JP-A-2003306487 and JP-A-11-152272). Hereinafter 1,3-dimethyl-2-imidazolidinone may also be referred to as DMI.

The objective compounds in the reactions are taken out, for example, by a method adding water and a water-insoluble organic solvent to the reaction mixture and extracting, a method adding water to the reaction mixture and crystallizing, and the like.

As DMI is very highly soluble in water, DMI is usually distributed in water layer and aqueous solution containing DMI in the case that water is used in the aftertreatment of the reaction as described above. From the industrial and environmental view, it is desired that DMI is recovered and reused from the aqueous solution without abandonment of the solution.

As a method recovering DMI from aqueous solution containing DMI described above, a method adding caustic alkali to the solution is known. However, after the recovery of DMI, the alkali solution generated should be neutralized before discarding.

SUMMARY OF THE INVENTION

An object of the present invention is to provide a process easily and efficiently recovering DMI at high purity from an aqueous solution containing DMI without using alkali.

Namely, the present invention relates to the followings.

<1> A process for recovering 1,3-dimethyl-2-imidazolidinone comprising extracting 1,3-dimethyl-2-imidazolidinone from an aqueous solution containing it with n-butanol in the presence of an inorganic salt to obtain n-butanol layer and, subjecting the n-butanol layer to distillation.

<2> The process according to <1>, wherein the inorganic salt is sodium chloride.

<3> The process according to <1> or <2>, wherein the amount of the inorganic salt is 0.05 to 0.2 part by weight per 1 part by weight of the aqueous solution.

<4> The process according to any of <1> to <3>, wherein the amount of the n-butanol is 0.2 to 1.5 parts by weight per 1 part by weight of the aqueous solution.

DETAILED DESCRIPTION OF PREFERRED EMBODIMENTS

The present process comprises extracting DMI from an aqueous solution containing DMI with n-butanol in the presence of an inorganic salt to obtain n-butanol layer and, subjecting the n-butanol layer to distillation.

In the present invention, the aqueous solution containing DMI may also contain other organic compounds or inorganic compounds. Examples of the aqueous solution include an aqueous layer containing DMI obtained by extracting, with water and water-insoluble solvent, a reaction mixture generated from an organic reaction using DMI; an aqueous filtrate containing DMI obtained after collecting crystals in a mixture obtained by adding water to a reaction mixture generated from an organic reaction using DMI; and the like.

The content of DMI in the aqueous solution is preferably 10% by weight or more for efficiently recovering DMI. The aqueous solution may be used as it is, or used after controlling the content of DMI, for example, by concentration.

The amount of n-butanol may be suitably determined depending on the content of DMI in the aqueous solution, and is usually 0.2 to 1.5 parts by weight, preferably 0.3 to 1 part by weight, more preferably 0.4 to 0.9 part by weight per 1 part by weight of the aqueous solution.

Though it may be conducted at a time, the extraction treatment is preferably conducted in two or more times with division of total amount of n-butanol for higher efficiency of extraction. When the extraction treatment is conducted in two or more times, number of times of extraction and amount of n-butanol per one time are not restricted. When the extraction treatment is conducted twice, first extraction is preferably conducted with 50 to 80% by weight of the total amount of n-butanol, and second extraction is conducted with the remainder of n-butanol, which is equal to 20 to 50% by weight of the total amount of n-butanol.

Examples of the inorganic salts include alkali metal chlorides such as sodium chloride and potassium chloride; alkali metal sulfonates such as sodium sulfonate and potassium sulfonate; alkali earth metal chloride such as calcium chloride; alkali metal bromide such as sodium bromide and potassium bromide; alkali earth metal bromide such as calcium bromide; and the like. The inorganic salts can be used each alone or in combination of two or more.

The amount of the inorganic salt is usually 0.05 to 0.2 part by weight per 1 part of the aqueous solution containing DMI for higher rate of recovery of DMI and for prevention of deposition of the inorganic salt.

When the aqueous solution containing DMI also originally contains inorganic salt, the amount of the inorganic salt to be added may be determined with taking it into consideration.

The extraction treatment is usually conducted by mixing the aqueous solution, the inorganic salt and n-butanol. The mixing may be a conventional method such as stirring with stirrer, shaking by shaker, and the like. The extraction temperature is usually 0 to 80° C., preferably 5 to 70° C.

After the extraction treatment, n-butanol layer containing DMI may be obtained. DMI can be recovered by subjecting the n-butanol layer to distillation.

The distillation treatment is usually conducted under reduced pressure. By the distillation treatment, a distillate mainly containing n-butanol is obtained first, and then, a distillate mainly containing DMI is obtained. The distillate mainly containing DMI may further be purified, for example, by rectification treatment. Alternatively, after evaporating the distillate mainly containing n-butanol from the n-butanol layer obtained by the extraction above, the concentrate may be subjected to rectification to obtain purified DMI. The distillate mainly containing n-butanol, as it is or after purification treatment such as rectification treatment, may be reused as the solvent for the present process.

It should be construed that embodiments disclosed here are examples in all aspects and not restrictive. It is intended that the scope of the present invention is determined not by the above descriptions but by appended Claims, and includes all variations of the equivalent meanings and ranges to the Claims.

The present invention will be further illustrated by examples. However, the present invention is not limited to them at all.

REFERENCE EXAMPLE 1

To a mixed solvent comprising 540 ml of DMI and 240 ml of toluene, 120 g of 1-(4-fluorophenyl)-1,3-dihydrobenzofuran-5-carbonitrile, 82 g of 3-(dimethylamino)propyl chloride and 24 g of 60% by weight of sodium hydride were added, and the mixture was maintained at 60° C. for reaction. After the reaction, to the reaction mixture, 700 g of 5% by weight of hydrochloric acid was added and mixed. The acid-added mixture was settled to separate into n-butanol layer and aqueous layer. The aqueous layer obtained was neutralized with 160 g of 25% by weight of sodium hydroxide. The neutralized aqueous layer was extracted twice with toluene (600 ml for first extraction and 240 ml for second extraction) to obtain 1330 g of aqueous solution containing DMI. By gas chromatography, it was determined that 436 g of DMI was contained in the solution.

EXAMPLE 1

To 900 ml of the aqueous solution containing DMI obtained in Reference Example 1, in which the amount of DMI was 295 g, 81 g of sodium chloride was added, and then, 360 g of n-butanol was further added. After the mixture was sufficiently stirred at room temperature, the stirred mixture was settled to separate n-butanol layer (1) and an aqueous layer. To the aqueous layer obtained, 180 g of n-butanol was added and the mixture was sufficiently stirred at room temperature, the stirred mixture was settled to separate n-butanol layer (2) and an aqueous layer. n-Butanol layer (1) and n-butanol layer (2) were combined to obtain 968 g of combined n-butanol layer. By gas chromatography, 284.2 g of DMI was contained in the combined n-butanol layer. The extraction rate was 96.3%.

The combined n-butanol layer containing DMI was subjected to distillation at the conditions of 80° C. of bath temperature and of 13.3 to 5.3 kPa (100 to 40 mmHg) of operation pressure to distill out n-butanol and obtain concentrate. The concentrate was subjected to rectification under reduced pressure (number of theoretical plate: 9) to obtain 196.5 g of DMI. Purity by gas chromatography was 99.8%. Rate of Recovery was 66.6%.

As DMI can be recoverable at high purity from an aqueous solution containing DMI by an easy method and without using alkali, the present process is industrially advantageous. Moreover, as n-butanol, the extraction solvent, can be re-usable, the present process is advantageous for environmental protection.

What is claimed is:

1. A process for recovering 1,3-dimethyl-2-imidazolidinone comprising extracting 1,3-dimethyl-2-imidazolidinone from an aqueous solution containing it with n-butanol in the presence of an inorganic salt to obtain n-butanol layer and, subjecting the n-butanol layer to distillation.

2. The process according to claim 1, wherein the inorganic salt is sodium chloride.

3. The process according to claim 1, wherein the amount of the inorganic salt is 0.05 to 0.2 part by weight per 1 part by weight of the aqueous solution.

4. The process according to claim 1, wherein the amount of the n-butanol is 0.2 to 1.5 parts by weight per 1 part by weight of the aqueous solution.

* * * * *